United States Patent
Jautelat et al.

(10) Patent No.: US 6,242,641 B1
(45) Date of Patent: *Jun. 5, 2001

(54) CYCLOALIPHATIC COMPOUNDS

(75) Inventors: Manfred Jautelat, Burscheid; Carl Casser, Berlin; Hanns-Peter Müller, Odenthal; Manfred Hajek, Leverkusen, all of (DE)

(73) Assignee: Bayer Aktiengesellschaft, Leverkusen (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/273,689

(22) Filed: Mar. 22, 1999

(30) Foreign Application Priority Data

Mar. 23, 1998 (DE) ............................................. 198 12 613

(51) Int. Cl.$^7$ .................................................. C07C 249/00
(52) U.S. Cl. ..................... 560/330; 560/336; 564/462; 564/461; 568/329; 568/721; 568/315
(58) Field of Search ..................... 564/461, 462; 560/330, 336; 568/329, 721, 315

(56) References Cited

U.S. PATENT DOCUMENTS 5,786,438  7/1998  Scholl et al. ..................... 528/67

FOREIGN PATENT DOCUMENTS 2225229  6/1998 (CA) .
19614269  10/1997 (DE) .
19650042  6/1998 (DE) .

OTHER PUBLICATIONS

Xiangdong He, et al, Journal of Applied Polymer Science, vol. 54, No. 2 Oct. 10, 1994, pp. 207–218.
Tanaka et al, Tetrahedron: Asymmetry, vol. 6, No. 6, Jun. 1, 1995, pp. 1273–1278.
Keana et al, Journal of Organic Chemistry, vol. 47, No. 2, Jan. 15, 1982, pp. 347–352.

*Primary Examiner*—Samuel Barts
(74) *Attorney, Agent, or Firm*—Joseph C. Gil; Thomas W. Roy

(57) ABSTRACT

The present invention relates to compounds selected from formula I

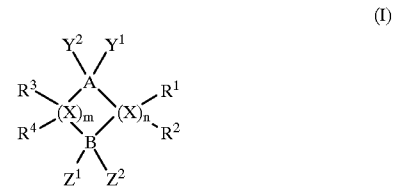

wherein
$R^1$, $R^2$, $R^3$ and $R^4$ are the same or different and represent hydrogen, $C_1$ to $C_6$-alkyl, $C_5$ to $C_6$-cycloalkyl, phenyl and halogen,
m and n are the same or different and represent the 2, 3, 4 or 5,
X, A and B represent carbon and
$Y^1$, $Y^2$, $Z^1$ and $Z^2$ are the same or different and represent hydrogen, hydroxyl (OH), amino ($NH_2$), isocyanato (NCO) or 4-hydroxyphenyl.

8 Claims, No Drawings

CYCLOALIPHATIC COMPOUNDS

FIELD OF THE INVENTION

The present invention relates to new cycloaliphatic compounds containing either isocyanate groups or isocyanate-reactive groups and to a process for their preparation.

SUMMARY OF THE INVENTION

The present invention relates to compounds corresponding to formula I

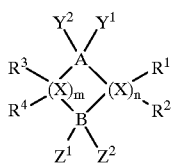

(I)

wherein
$R^1$, $R^2$, $R^3$ and $R^4$ are the same or different and represent hydrogen, $C_1$ to $C_6$-alkyl, $C_5$ to $C_6$-cycloalkyl, phenyl and halogen,
m and n are the same or different and represent the 2, 3, 4 or 5,
X, A and B represent carbon and
$Y^1$, $Y^2$, $Z^1$ and $Z^2$ are the same or different and represent hydrogen, hydroxyl (OH), amino ($NH_2$), isocyanato (NCO) or 4-hydroxyphenyl,
provided that
1) on at least one atom X one of the pairs, either $R^1$ and $R^2$ or $R^3$ and $R^4$, are both alkyl and
2) if $Y^1$ and $Y^2$ each represent 4-hydroxyphenyl, then $Z^1$ represents hydroxyl (OH) and $Z^2$ represents hydrogen or $Z^1$ and $Z^2$ together denote an oxo group (=O) and
3) if one $Y^1$, $Y^2$, $Z^1$ or $Z^2$ is isocyanato (NCO) the remaining groups cannot represent hydroxyl (OH), amino ($NH_2$) or 4-hydroxyphenyl and
4) if $Y^1$ or $Y^2$ denotes hydroxy (OH), $Z^1$ and $Z^2$ are not hydroxy (OH) or hydrogen (H) and
5) if $Z^1$ or $Z^2$ are hydroxy (OH), $Y^1$ and Y2 are not hydroxy (OH) or hydrogen (H) and
6) if $Y^1$ or $Y^2$ denotes amino ($NH_2$), $Z^1$ and $Z^2$ are not hydrogen (H) and
7) if $Z^1$ or $Z^2$ are amino ($NH_2$), $Y^1$ and $Y^2$ are not hydrogen (H).

The present invention also relates to a process for the preparation of these compounds.

DETAILED DESCRIPTION OF THE INVENTION

Preferably, on 1 to 2 X atoms, more preferably on only one X atom, either $R^1$ and $R^2$ or $R^3$ and $R^4$ both represent alkyl. The preferred alkyl radical is methyl. Preferably, the sum of n and m is four, and in particular m and n are each two. More preferably, m and n are each two and only the X atoms in the α-position to a carbon atom A or B are substituted by two alkyl groups. Preferably, only one carbon atom, A or B, is substituted by two 4-hydroxyphenyl groups. Preferably, the compounds are difunctional, i.e., they contain two isocyanate-reactive groups or two isocyanate groups.

Preferred cycloalkane derivatives correspond to the formulas

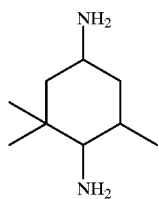

(Ia)

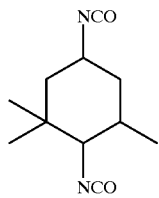

(Ib)

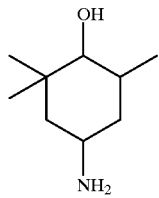

(Ic)

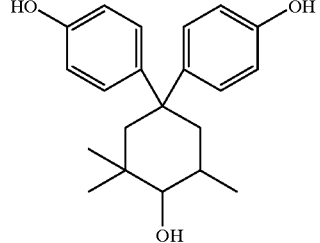

(Id)

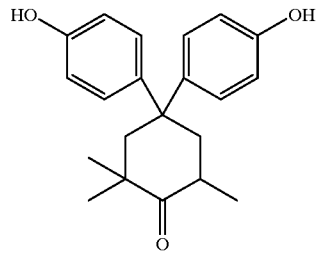

(Ie)

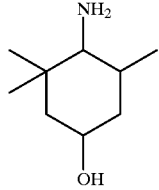

(If)

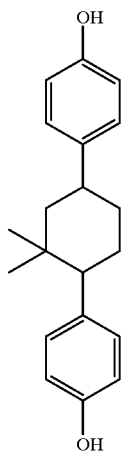

(Ig)

The most preferred cycloalkane derivatives are 1,4-diamino-2,2,6-trimethylcyclohexane (formula Ia), 1,4-diisocyanato-2,2,6-trimethylcyclohexane (formula Ib), 1-hydroxy-2,2,6-trimethyl-4-aminocyclohexane (formula Ic), 1,1-bis-(4-hydroxyphenyl)- 3,3,5-trimethyl-4-hydroxycyclohexane (formula Id) and 1,1-bis-(4-hydroxyphenyl)-3,3,5-trimethyl-4-oxocyclohexane (formula Ie).

The compounds of the formula I can be prepared in known manner, e.g., by the reductive amination of the diketones of formula II or III

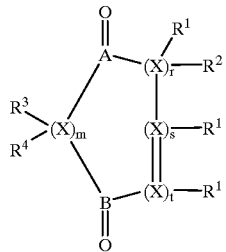

(II)

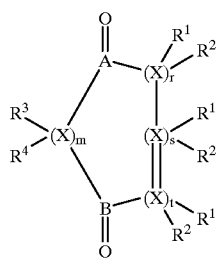

(III)

wherein
$R^1$, $R^2$, $R^3$, $R^4$, X, A, B, m and n are as defined in formula I and
r, s and t are the same or different and represent the number 0, 1, 2, 3, 4 or 5, provided that the sum of r, s and t is n.

Using the preceding method, diamino compounds corresponding to formula I wherein $Y^1$ and $Z^1$ both represent amino ($NH_2$) and $Y^2$ and $Z^2$ both represent hydrogen may be obtained.

Suitable cycloalkane derivatives also include aminoalcohols corresponding to formula (IV)

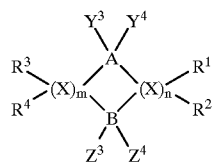

(IV)

wherein
$R^1$, $R^2$, $R^3$, $R^4$, X, A, B, m and n are as defined in formula I,
$Y^3$ and $Z^3$ denote hydrogen and
either $Y^4$ and $Z^4$ represents amino ($NH_2$), while the other represents hydroxyl (OH) may also be obtained from the starting materials of formula II or III.

Aminoalcohols corresponding to formula IV may also be obtained by reductive amination of the hydroxy-ketones of formula V or VI

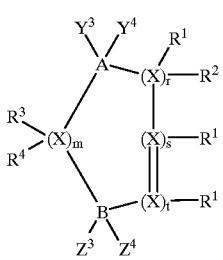

(V)

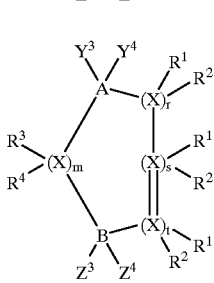

(VI)

wherein
$R^1$, $R^2$, $R^3$, $R^4$, X, A, B, m, n, r, s and t are as defined in formulas I, II and III and either
$Y^3$ and $Y^4$ together represent an oxo group (=O), $Z^3$ represents hydroxyl (OH) and $Z^4$ represents hydrogen, or
$Z^3$ and $Z^4$ together represent an oxo group (=O), $Y^3$ represents hydroxyl and $Y^4$ represents hydrogen.

The diketones of the formula II, III and the hydroxyketones of formula V and VI are known and described, e.g., in K. Mori, Tetrahedron vol. 30, 1065–1072 (1974), J. N. Marx, F. Sondheimer, Tetrahedron, Supp. 8, part I, 1–7 (1966), H. G. W. Leuenberger, W. Boguth, E. Widmer, R. Zell, Helvetica Chimica Acta, vol. 59, 1832–1849, (1976) and DE-A 2,4 57,158.

The reductive amination of ketones is also known and described, e.g., by W. Schneider, K. Lehmann in Methodicum Chimicum, volume 6, page 536 et seq. and R. Schröter, F. Möller in Houben-Weyl, volume XI/1, page 602 et seq. Further details for carrying out the reductive amination are found in DE 3,031,955, 3,011,656, 1,226,078 and 4,033,609. Suitable hydrogenation catalysts include Raney nickel, Raney cobalt, Pt or Pd. The reaction can be carried out at temperatures of 50 to 200° C. and pressures of 10 to 250 bar, optionally in the presence of a solvent and/or dehydrating agent.

Particularly preferred diketones of formula II and III and particularly preferred hydroxy-ketones of formula V and VI are compounds corresponding to the formula

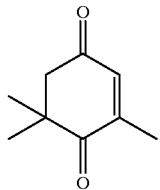
(IIa)

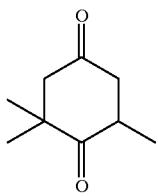
(IIIa)

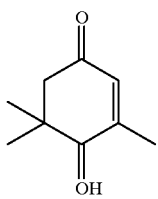
(Va)

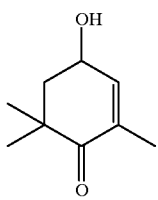
(Vb)

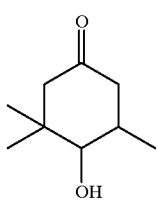
(VIa)

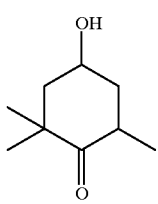
(VIb)

The amino-alcohols of formula IV can also be obtained by the catalytic hydrogenation of imines corresponding to formula VII or VIII

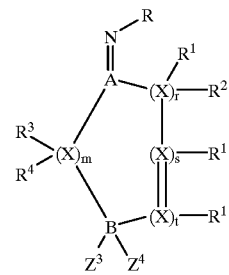
(VII)

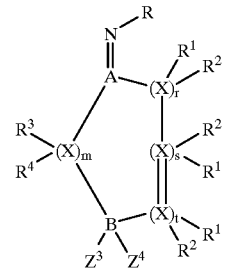
(VIII)

wherein
$R^1$, $R^2$, R $R^3$, $R^4$, X, A, B, m, n, r, s and t are as defined in formulas I, II, III, V and VI
$Z^3$ represents hydrogen and $Z^4$ represents hydroxyl (OH) or $Z^3$ and $Z^4$ together represent an oxo group (=O) and
R represents hydrogen, benzyl, hydroxyl or a radical corresponding to formula IX or X

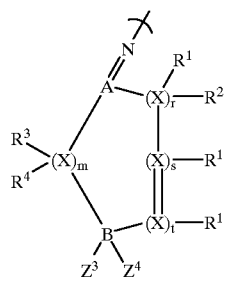
(IX)

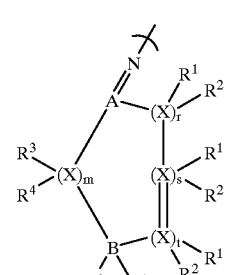
(X)

wherein
$R^1$, $R^2$, $R^3$, $R^4$, X, A, B, m, n, $Z^3$, $Z^4$, r, s and t are as defined in formula VII and VIII.

The diamino compounds corresponding to formula I wherein $Y^1$ and $Z^1$ both represent amino ($NH_2$) and $Y^2$ and $Z^2$ both represent hydrogen may also be obtained by reductive amination of the imines of formula VII or VIII.

The imines of the general formula (VII) and (VIII) are accessible by methods known from the literature by reaction of the ketones of the general formulas (II), (III), (V) and (VI) with amine derivatives, such as e.g. ammonia, hydrazine, hydroxylamine and benzylamine (see, for example, Houben-Weyl, volume X/2, page 85 et seq. and volume 7/2b, page 1944 et seq.).

Preferred imines of the general formula (VII) and (VIII) are the compounds

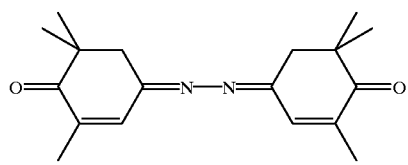
(VIIa)

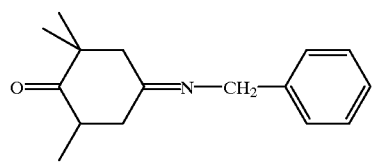
(VIIIa)

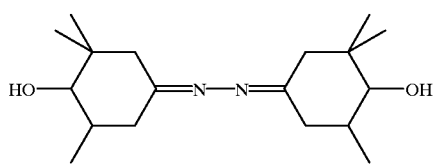
(VIIIb)

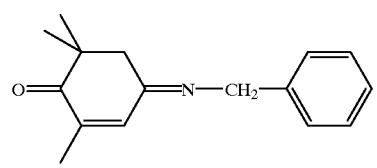
(VIIb)

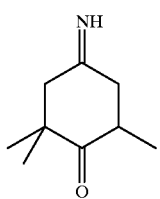
(VIIIc)

The diisocyanato compounds of formula I wherein $Y^1$ and $Z^1$ both represent isocyanato (NCO) and $Y^2$ and $Z^2$ both represent hydrogen can be prepared by the phosgenation of the corresponding diamino compounds of formula I wherein $Y^1$ and $Z^1$ both represent amino ($NH_2$) and $Y^2$ and $Z^2$ both represent hydrogen by known methods as described, e.g., in Houben-Weyl, volume VIII, page 119 et seq.

The dihydroxydiphenylcycloalkanes corresponding to formula I wherein
$Y^1$ and $Y^2$ both represent 4-hydroxyphenyl and either
$Z^1$ $Z^2$ represents hydrogen and $Z^2$ represents hydroxyl (OH)
or
$Z^1$ and $Z^2$ together represent oxo grouping (=O) can be prepared in a known manner by the condensation of phenol with ketones corresponding to formulas II and V, wherein s and t are zero, in the presence of acid catalysts and optionally by addition of sulfur-containing co-catalysts. This condensation reaction is described, e.g., in Schnell, Chemistry and Physics of Polycarbonates, Inter-science Publishers, New York 1964 and in EP-A 359,953 and U.S. Pat. No. 5,210,328.

The compounds of the formula I are valuable intermediate products for the preparation and modification of polymers, such as polycarbonates, polyamides, polyureas and polyurethanes as described, e.g., in Houben-Weyl, volume E20, part 2.

The invention is further illustrated but is not intended to be limited by the following examples in which all parts and percentages are by weight unless otherwise specified.

EXAMPLES

Example 1

1,4-diamino-2,2,6-trimethylcyclohexane (formula Ia)

A mixture of 152 g of 4-oxoisophorone (formula IIa), 150 g of ammonium sulfate, 50 g of Raney Ni and 1 liter of ammonia was charged with 80 bar hydrogen in a 3 liter autoclave at room temperature and then stirred at 180° C. for 20 h. When the uptake of hydrogen was complete, the reaction mixture was let down, taken up in ethanol, filtered and subjected to fractional distillation. 130 g of the diamine of formula Ia having a boiling point of 62 to 65° C. under 0.1 mbar were obtained.

Example 2

1,4-diamino-2,2,6-trimethylcyclohexane (formula Ia)

25 g of hydrazine hydrate in 30 ml of ethanol were added to 152 g of 4-oxoisophorone (formula IIa) in 125 ml ethanol over a period of 30 min. The reaction mixture was boiled under reflux for 12 h and concentrated to half the volume, and the ketazine product (133 g, m.p. 132° C.) of formula VIIa, which precipitated out, was filtered off. The ketazine derivative VIIa can be used as a starting material without further purification.

150 g of ketazine derivative VIIa, 140 g of ammonium sulfate and 25 g of Ra/Ni/Co in 1 liter of ammonia were hydrogenated analogously to example 1. After working up analogously to example 1, 135 g of the diamine of formula Ia were obtained.

Example 3

1-amino-3,3,5-trimethyl-4-hydroxycyclohexane (formula Ic)

156 g of 3,3,5-trimethyl-4-hydroxycyclohexanon (formula VIa), 12 g of ammonium acetate and 60 g of Raney Ni in 250 ml methanol were hydrogenated at 100° C. under a hydrogen pressure of 100 bar in the presence of 250 ml of ammonia. When the uptake of hydrogen was complete, the catalyst was filtered off, the filtrate was concentrated under vacuum and the residue was subjected to fractional distillation under a high vacuum. 130 g of the aminoalcohol of formula Ic, which had a melting point of 110 to 112° C., were obtained at 90 to 97° C. (0.1 mbar). According to analysis by gas chromatography, an isomer mixture (four isomers) was present.

Example 4

1-amino-3,3,5-trimethyl-4-hydroxycyclohexane (formula Ic)

A solution of 60 g of the ketazine derivative of formula VIIa from example 2, 8 ml of triethylamine and 400 ml of methanol was hydrogenated in the presence of 24 g of Ra/Ni at 140° C. under a hydrogen pressure of 150 bar until the uptake of hydrogen was complete. After working up analogously to example 3, 51 g of the aminoalcohol of formula Ic were obtained.

Example 5
1,4-diisocyanato-3,3,5-trimethylcyclohexane (formula Ib)

A solution of 156 g of the diamine of formula (Ia) in 250 g, of chlorobenzene was added dropwise to a solution of 500 g of phosgene in 3 liter of chlorobenzene at 0 to 10° C. The reaction mixture was heated to 120° C. with further introduction of phosgene, and phosgenation was carried out at this temperature until the clear point was reached. Excess phosgene and chlorobenzene were distilled off under vacuum and the residue which remained was subjected to fractional distillation. 167 g of the diisocyanate of formula Ib were obtained at 84 to 87° C. (0.1 to 0.3 mbar). According to analysis by $^1$H spectroscopy, an isomer mixture of four isomers was obtained.

Example 6
1,1-bis-(4-hydroxyphenyl)-3,3,5-trimethyl-4-oxocyclohexane (formula Ie)

6 ml of concentrated hydrochloric acid were added to 8 g of 3,3,5-trimethyl 1,4-dioxocyclohexane (formula IIIa), 30 g of phenol and 0.5 ml β-mercaptopropionic acid and the mixture was stirred at 30° C. until the conversion (monitoring by gas chromatography) of the diketone was complete. Excess phenol was extracted with water and the residue was washed several times with toluene and n-hexane at 60° C. 6 g of the bisphenol (m.p.: 140° C.) of formula Ie remained.

IR (KBr): 3600 to 3100 cm$^{-1}$ (OH), 1680 cm$^{-1}$ (CO).

Example 7
1,1-Bis-(4-hydroxyphenyl)-3,3,5-trimethyl-4-hydroxycyclo-hexane (formula Id)

Example 6 was repeated with the exception that 10 g of the hydroxyketone of formula VIa were used instead of 8 g of the diketone of formula IIIa. 5 g of the bisphenol of formula Id were obtained-m.p.: 102° C. (decomp.). According to analysis by $^1$H spectroscopy, the product contained two isomers (77/23). In the main isomer the OH function was arranged axially and the 5-CH$_3$ group equatorially.

Example 8

According to example 1 of application DE 19 653 585.9 of the applicant company, which has not yet been published, an aqueous polyurethane dispersion which was free from co-solvent was prepared.

Comparison Example
(DE 19 653 585, U.S. Ser. No. 09/989,065)

170 g (0.1 mole) of a polyester prepared from adipic acid, 1,6-hexanediol and neopentyl glycol (65:35 molar ratio of diols) and having a number average molecular weight of 1,700 and an OH content of 2% were dehydrated in a reaction vessel at 120° C. under 10 mbar for 30 minutes with stirring. 13.4 g (0.1 mole) of dimethylol-propionic acid and 111 g (0.5 mole) of isophorone diisocyanate were introduced under nitrogen. After a reaction time of 1 hour at 110° C., the batch was cooled to 60° C. and dissolved in 100 g of acetone. After addition of 18 g (0.2 mole) of 1,4-butane-diol, the mixture was subsequently stirred at 50° C. for 22 hours, and diluted with 500 g of acetone. A mixture of 10.6 g (0.062 mole) of isophorone diamine, 1.07 g (0.016 mole) of 25% ammonia solution and 60 g of water was added to the NCO prepolymer at 50° C. The mixture was then subsequently stirred at 50° C. for 5 hours. It was neutralized with 3.4 g (0.05 mole) of a 25% ammonia solution and dispersed with 450 g of water. The acetone was removed up to 50° C. and 150 mbar, to give a white dispersion having a solids content of 39.2% and an average particle size of 263 nm.

A wet film was drawn down onto a glass plate with a 200 μm doctor blade and was then dried in a drying cabinet at 80° C. for 10 minutes. The resulting film had a dry film thickness of 70 to 80 μm. The dry film was peeled off the glass and the tensile properties were determined in accordance with DIN 53 455.

Example According to the Invention

The preparation of the preceding aqueous polyurethane dispersion was repeated with the exception that 0.062 moles of 1,4-diamino-2,2,6-trimethylcyclohexane (formula Ia) were employed instead of 0.062 moles of isophorone diamine.

After the preparation of the aqueous dispersion, a wet film was drawn down onto a glass plate with a 200 μm doctor blade and was then dried in a drying cabinet at 80° C. The resulting film also had a dry film thickness of 70 to 80 μm. The dry film was peeled off the glass and the tensile properties were determined in accordance with DIN 53 455.

The E modulus of the film produced with the diamine from formula Ia according to the invention was 30% higher and the yield stress or elongation was 10% higher than that of the comparison.

Example 9

67.2 g (0.4 mole) of 1,6-hexamethylene diisocyanate were dissolved in 40 g of acetone. 15.7 g (0.1 mole) of amino alcohol of formula Ic according to the invention were introduced into this solution with stirring. During the addition, the mixture heated up to 40° C. The mixture was heated to 66° C. over a period of 75 minutes. A clear solution was formed. A vacuum was then applied and the acetone was stripped off. The NCO content was determined from a sample of the product.

The NCO content of the product was 30.3%. The product was then stirred under nitrogen at 140 to 150° C. for a further 30 minutes. The resulting modified polyisocyanate had an NCO content of 22.1%. The IR spectrum indicated the presence of biuret groups.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A compound corresponding to formula I

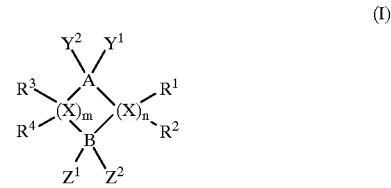

wherein
  R$^1$, R$^2$, R$^3$ and R$^4$ are the same or different and represent hydrogen, C$_1$ to C$_6$-alkyl, C$_5$ to C$_6$-cycloalkyl, phenyl and halogen,
  m and n are the same or different and represent the 2, 3, 4 or 5,
  X, A and B represent carbon and
  Y$^1$, Y$^2$, Z$^1$ and Z$^2$ are the same or different and represent hydrogen, hydroxyl (OH), amino (NH$_2$), isocyanato (NCO) or 4-hydroxyphenyl, provided that
1) on one, but not both X atoms, atom X one of the pairs, either $R^1$ and $R^2$ or $R^3$ and $R^4$, are both alkyl and
2) if $Y^1$ and $Y^2$ each represent 4-hydroxyphenyl, then $Z^1$ represents hydroxyl (OH) and $Z^2$ represents hydrogen or $Z^1$ and $Z^2$ together denote an oxo group (=O);
3) if one $Y^1$, $Y^2$, $Z^1$ or $Z^2$ is isocyanato (NCO) the remaining groups cannot represent hydroxyl (OH), amino ($NH_2$) or 4-hydroxyphenyl and
4) if $Y^1$ or $Y^2$ denotes hydroxy (OH), $Z^1$ and $Z^2$ are not hydroxy (OH) or hydrogen (H) and
5) if $Z^1$ or $Z^2$ are hydroxy (OH), $Y^1$ and $Y^2$ are not hydroxy (OH) or hydrogen (H);
6) if $Y^1$ or $Y^2$ denotes amino ($NH_2$), $Z^1$ and $Z^2$ are not hydrogen (H) and
7) if $Z^1$ or $Z^2$ are amino ($NH_2$), $Y^1$ and $Y^2$ are not hydrogen (H).

2. The compound of claim 1 wherein $R^1$, $R^2$, $R^3$ and $R^4$ are the same or different and represent hydrogen or methyl and m and n each represent 2.

3. The compound of claim 1 wherein the compound of formula I is 1,4-diamino-2,2,6-trimethylcyclohexane.

4. The compound of claim 1 wherein the compound of formula I is 1,4-diisocyanato-2,2,6-trimethylcyclohexane.

5. The compound of claim 1 wherein the compound of formula I is 1-hydroxy-2,2,6-trimethyl-4-aminocyclohexane.

6. The compound of claim 1 wherein the compound of formula I is 1,1-bis-(4-hydroxyphenyl)-3,3,5-trimethyl-4-oxocyclohexane.

7. The compound of claim 1 wherein the compound of formula I is 1,1-bis-(4-hydroxyphenyl)-3,3,5-trimethyl-4-hydroxycyclohexane.

8. A process for the preparation of the compound corresponding to formula I

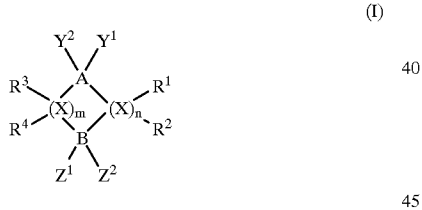

(I)

wherein
$R^1$, $R^2$, $R^3$ and $R^4$ are the same or different and represent hydrogen, $C_1$ to $C_6$-alkyl, $C_5$ to $C_6$-cycloalkyl, phenyl and halogen,
m and n are the same or different and represent the 2, 3, 4 or 5,
X, A and B represent carbon and
$Y^1$, $Y^2$, $Z^1$ and $Z^2$ are the same or different and represent hydrogen, hydroxyl (OH), amino ($NH_2$),
provided that
1) on one, but not both X atoms, atom X one of the pairs, either $R^1$ and $R^2$ or $R^3$ and $R^4$, are both alkyl and
2) that two groups of $Z^1$, $Z^2$, $Y^1$ and $Y^2$ represent hydroxyl (OH) or amino ($NH_2$) and
3) if $Y^1$ or $Y^2$ denotes hydroxyl (OH), $Z^1$ and $Z^2$ are not hyroxyl (OH or hydrogen (H) and
4) if $Z^1$ or $Z^2$ are hydroxyl (OH), $Y^1$ and $Y^2$ are not hydroxyl (OH) or hydrogen (H),
which comprises reacting a compound corresponding to formula V or VI

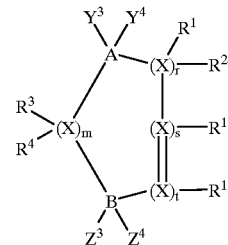

(V)

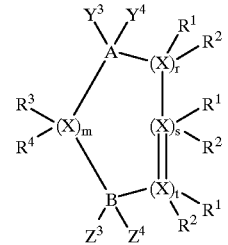

(VI)

wherein
r, s and t are the same or different and represent the number 0, 1, 2, 3, 4 or 5, provided that the sum of r, s and t is n,
$Y^3$ and $Y^4$, and $Z^3$ and $Z^4$ each represent an oxo group or
$Y^3$ and $Y^4$ represent an oxo group, $Z^3$ represents hydroxyl and $Z^4$ represents hydrogen,
$Z^3$ and $Z^4$ represent an oxo group, $Y^3$ represents hydroxyl and $Y^4$ represents hydrogen, or
$Y^3$ and $Y^4$ represent an imino group (=N—R), $Z^3$ represents a hydroxyl group and $Z^4$ represents hydrogen or $Z^3$ and $Z^4$ represent an oxo group, and
R represents hydrogen, benzyl, hydroxyl or a group corresponding to formula IX or X

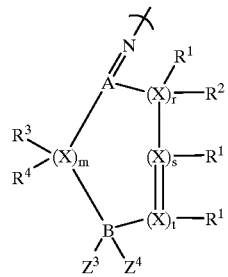

(IX)

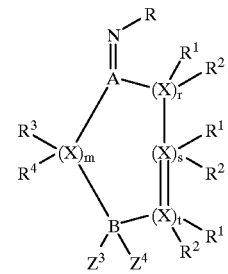

(X)

with hydrogen and optionally with ammonia in the presence of a hydrogenation catalyst at temperatures of 50 to 200° C. and pressures of 10 to 250 bar.

* * * * *